US010444153B2

(12) United States Patent
Kim

(10) Patent No.: US 10,444,153 B2
(45) Date of Patent: Oct. 15, 2019

(54) SPECTRUM MEASUREMENT APPARATUS AND SPECTRUM MEASUREMENT METHOD

(71) Applicant: SAMSUNG ELECTRONICS CO., LTD., Suwon-si (KR)

(72) Inventor: Sang Kyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/885,035

(22) Filed: Jan. 31, 2018

(65) Prior Publication Data
US 2019/0033217 A1 Jan. 31, 2019

(30) Foreign Application Priority Data
Jul. 25, 2017 (KR) .................. 10-2017-0094311

(51) Int. Cl.
| G01N 21/65 | (2006.01) |
| G01N 21/66 | (2006.01) |
| G01J 3/44 | (2006.01) |
| G01J 3/10 | (2006.01) |
| G01J 3/42 | (2006.01) |
| G01J 3/02 | (2006.01) |
| G01N 21/359 | (2014.01) |
| G01J 3/12 | (2006.01) |
| G01N 21/47 | (2006.01) |

(52) U.S. Cl.
CPC ............. *G01N 21/65* (2013.01); *G01J 3/027* (2013.01); *G01J 3/10* (2013.01); *G01J 3/42* (2013.01); *G01J 3/44* (2013.01); *G01J 3/4412* (2013.01); *G01N 21/359* (2013.01); *G01N 21/66* (2013.01); *G01J 2003/1282* (2013.01); *G01J 2003/4418* (2013.01); *G01N 21/4738* (2013.01)

(58) Field of Classification Search
CPC ....... G01N 21/65; G01N 21/66; G01J 3/4412; G01J 2003/4418
See application file for complete search history.

(56) References Cited

U.S. PATENT DOCUMENTS

| 4,225,223 A | 9/1980 | Papadakis | |
| 4,620,284 A * | 10/1986 | Schnell | G01N 21/65 356/301 |
| 7,057,712 B2 * | 6/2006 | Beck | G01N 15/1459 250/288 |
| 7,087,901 B2 | 8/2006 | Ambuel | |
| 7,106,763 B2 | 9/2006 | Tan et al. | |

(Continued)

FOREIGN PATENT DOCUMENTS

| JP | 2000-9644 A | 1/2000 |
| KR | 2003-0019735 A | 3/2003 |
| KR | 10-2010-0043768 A | 4/2010 |

*Primary Examiner* — Dominic J Bologna
(74) *Attorney, Agent, or Firm* — Sughrue Mion, PLLC

(57) ABSTRACT

A spectrum measurement apparatus includes: a plurality of light sources configured to emit light having different wavelengths to an object; a light detector configured to receive light, which is reflected or scattered from or transmitted through the object, and to measure an intensity of the received light; and a processor configured to determine a strength of an electric signal to be applied to at least one of the plurality of light sources by using one of the plurality of light sources, and by applying the electric signal having the determined strength to the plurality of light sources to obtain a spectrum of the object.

14 Claims, 11 Drawing Sheets

(56) References Cited

U.S. PATENT DOCUMENTS

| | | | |
|---|---|---|---|
| 7,113,282 B2* | 9/2006 | Aguirre | G01J 1/20 |
| | | | 356/418 |
| 7,214,927 B2* | 5/2007 | Lim | H05B 33/0869 |
| | | | 250/229 |
| 7,245,373 B2 | 7/2007 | Soller et al. | |
| 9,250,132 B2 | 2/2016 | Bonyuet et al. | |
| 9,291,502 B2 | 3/2016 | Nishimura | |
| 9,297,997 B2 | 3/2016 | Sano | |
| 2004/0036862 A1* | 2/2004 | Liang | G01N 21/6489 |
| | | | 356/237.2 |
| 2006/0215177 A1* | 9/2006 | Doerband | G01B 11/2509 |
| | | | 356/609 |
| 2006/0280216 A1 | 12/2006 | Jayaraman | |
| 2007/0029514 A1* | 2/2007 | Buisker | B65H 23/0216 |
| | | | 250/559.36 |
| 2010/0084557 A1* | 4/2010 | Koay | A61B 5/0059 |
| | | | 250/339.07 |
| 2011/0026015 A1* | 2/2011 | Mimeault | G01F 23/292 |
| | | | 356/139.1 |
| 2012/0092670 A1* | 4/2012 | Chatow | G01J 3/501 |
| | | | 356/402 |
| 2016/0116399 A1 | 4/2016 | Hruska et al. | |
| 2017/0370828 A1* | 12/2017 | Arifin | G01N 21/31 |
| 2018/0106712 A1* | 4/2018 | Owen | G01N 15/0211 |

\* cited by examiner

SPECTRUM MEASUREMENT APPARATUS AND SPECTRUM MEASUREMENT METHOD

CROSS-REFERENCE TO RELATED APPLICATION(S)

This application claims priority from Korean Patent Application No. 10-2017-0094311, filed on Jul. 25, 2017 in the Korean Intellectual Property Office, the entire disclosure of which is incorporated herein by reference.

BACKGROUND

1. Field

Apparatuses and methods consistent with exemplary embodiments relate generally to technology for spectrum measurement, and more particularly, to an apparatus and a method for measuring a spectrum of a sample having various reflectance levels by adjusting an electric signal applied to a light source.

2. Description of the Related Art

A spectrometer is an efficient instrument which detects light reflected or scattered from or transmitted through a sample, and analyzes the composition of the sample to determine properties of the sample, in which it is required to maximize a signal to noise ratio (SNR) of the spectrum of the sample to accurately measure and analyze a minute amount of sample.

Accordingly, in order to improve the performance of the spectrometer, there is a need to optimize the spectrum reconstruction algorithm and a parameter used for the algorithm.

In order to measure the spectrum of a sample having various reflectance levels, the spectrometer generally sets the gain of a light detector based on a sample having high reflectance, or according to a reflectance level of a specific sample. In this case, however, when measuring a spectrum of a sample having a higher reflectance level than the reflectance of the specific sample, a signal of the light detector is saturated, such that it is difficult to measure the spectrum of the sample; and when measuring a spectrum of a sample having a lower reflectance level than the reflectance of the specific sample, a signal is weak, such that the SNR of the spectrum of the sample becomes smaller.

SUMMARY

One or more exemplary embodiments provide a spectrum measurement apparatus and a spectrum measurement method which may measure a sample having various reflectance levels by adjusting an electric signal applied to a light source.

According to an aspect of an exemplary embodiment, there is provided a spectrum measurement apparatus including: a plurality of light sources configured to emit light having different wavelengths to an object; a light detector configured to receive light, which is reflected or scattered from or transmitted through the object, and to measure an intensity of the received light; and a processor configured to determine a strength of an electric signal to be applied to at least one of the plurality of light sources by using one of the plurality of light sources, and to obtain a spectrum of the object by applying the electric signal having the determined strength to the at least one of the plurality of light sources.

The light detector may amplify the received light according to a predetermined gain.

The processor may select a light source, having a largest amount of light, among the plurality of light sources, and may determine the strength of the electric signal to be applied to the at least one of the plurality of light sources by using the selected light source.

Based on the measured intensity of the light detector that is obtained by applying the electric signal having various strengths to the selected light source, the processor may determine a range of the strength of the electric signal in which the light detector is not saturated, and may determine a highest value in the range of the strength of the electric signal to be the strength of the electric signal to be applied to the at least one of the plurality of light sources.

The processor may obtain the measured intensity of the light detector, which corresponds to each of the plurality of light sources, by applying the electric signal having the determined strength to the plurality of light sources, obtain a light spectrum corresponding to each of the plurality of light sources, and may obtain the spectrum of the object by using the measured intensity and the light spectrum corresponding to each of the plurality of light sources.

The light spectrum corresponding to each of the plurality of light sources may be a spectrum of light emitted from each of the plurality of light sources when the electric signal having various strengths is applied to each of the plurality of light sources.

The processor may obtain the light spectrum corresponding to each of the plurality of light sources from at least one of an internal database and an external database, or by applying the electric signal having various strengths to each of the plurality of light sources and measuring the intensity of light emitted from each of the plurality of light sources.

The spectrum measurement apparatus may further include a light amount adjuster configured to adjust the strength of the electric signal to be applied to the at least one of the plurality of light sources according to a control signal of the processor.

According to an aspect of another exemplary embodiment, there is provided a spectrum measurement method of a spectrum measurement apparatus comprising a plurality of light sources and a light detector, the method including: determining a strength of an electric signal to be applied to at least one of the plurality of light sources by using one of the plurality of light sources; and obtaining a spectrum of an object by applying the electric signal having the determined strength to the at least one of plurality of light sources.

The determining of the strength of the electric signal to be applied to at least one of the plurality of light sources may include: selecting a light source, having a largest amount of light, among the plurality of light sources; emitting light to the object by applying an electric signal having various strengths to the selected light source, and measuring, by the light detector, an intensity of light reflected or scattered from or transmitted through the object; based on the measured intensity, determining a range of the strength of the electric signal in which the light detector is not saturated; and determining a highest value in the range of the strength of the electric signal to be a strength of the electric signal to be applied to at least one of the plurality of light sources.

The obtaining of the spectrum of the object may include: emitting light to the object by applying the electric signal having the determined strength to the at least one of the plurality of light sources, and measuring, by the light detector, an intensity of light reflected or scattered from or transmitted through the object; and obtaining the spectrum of the object by using the measured intensity and a light spectrum corresponding to each of the plurality of light sources.

The light spectrum corresponding to each of the plurality of light sources may be a spectrum of light emitted from each of the plurality of light sources when the electric signal having various strengths is applied to each of the plurality of light sources.

The spectrum measurement method may further include obtaining the light spectrum corresponding to each of the plurality of light sources from at least one of an internal database and an external database.

The spectrum measurement method may further include: applying the electric signal having the various strengths to each of the plurality of light sources; and obtaining the light spectrum corresponding to each of the plurality of light sources by measuring the intensity of light emitted from each of the plurality of light sources.

According to an aspect of still another exemplary embodiment, there is provided a composition analysis apparatus, including: a spectrum measurer configured to obtain a spectrum of an object; and a first processor configured to analyze the spectrum of the object to analyze a composition of the object, wherein the spectrum measurer may include: a plurality of light sources configured to emit light having different wavelengths to the object; a light detector configured to receive light, which is reflected or scattered from or transmitted through the object, and to measure an intensity of the received light; and a second processor configured to determine a strength of an electric signal to be applied to at least one of the plurality of light sources by using one of the plurality of light sources, and to obtain the spectrum of the object by applying the electric signal having the determined strength to the at least one of the plurality of light sources.

BRIEF DESCRIPTION OF THE DRAWINGS

The above and/or other aspects will become apparent and more readily appreciated from the following description of the exemplary embodiments, taken in conjunction with the accompanying drawings in which.

DETAILED DESCRIPTION

Figure 1:
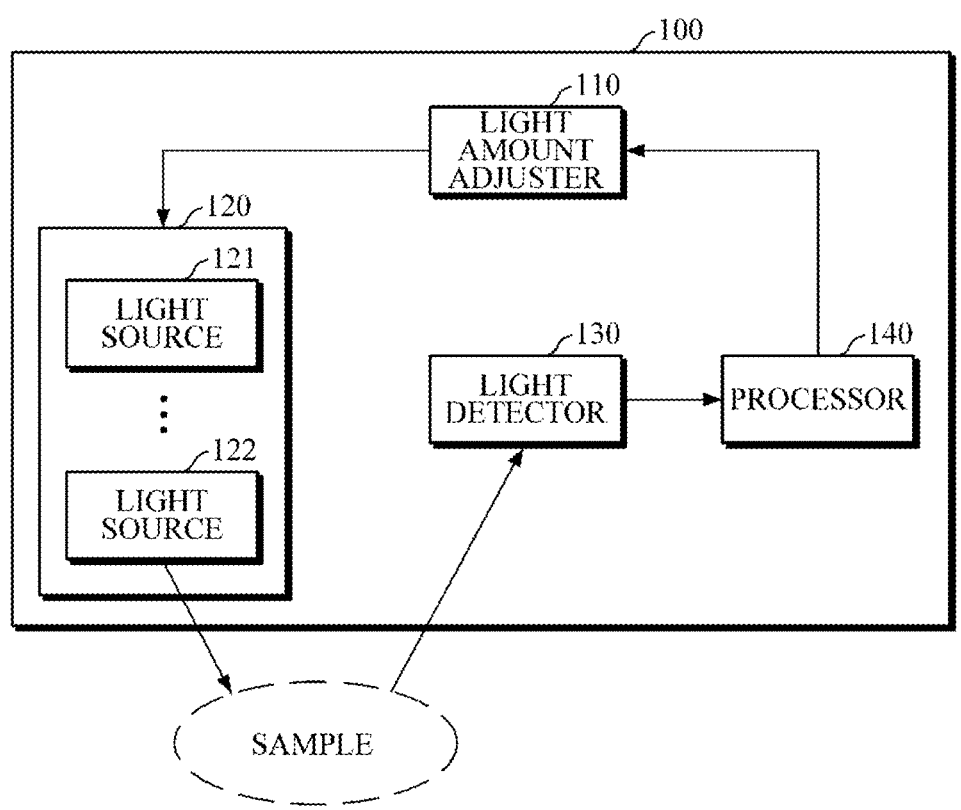
FIG. 1 is a block diagram illustrating a spectrum measurement apparatus according to an exemplary embodiment.

Hereinafter, the exemplary embodiments will be described in detail with reference to the accompanying drawings. It should be noted that, in the drawings, the same reference symbols refer to same parts although illustrated in other drawings.

Throughout the drawings and the detailed description, unless otherwise described, the same drawing reference numerals will be understood to refer to the same elements, features, and structures. The relative size and depiction of these elements may be exaggerated for clarity, illustration, and convenience. In the following description, a detailed description of known functions and configurations incorporated herein will be omitted when it may obscure the subject matter of the disclosure.

Process steps described herein may be performed differently from a specified order, unless the specified order is clearly stated in the context of the disclosure. That is, each step may be performed in a specified order, at substantially the same time, or in a reverse order.

Further, the terms used throughout the specification are defined in consideration of the functions according to exemplary embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'comprises,' 'comprising,' 'includes,' 'including' and/or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Herein, the expression, "at least one of a and b," should be understood as including only a, only b, or both a and b. Similarly, the expression, "at least one of a, b, and c," should be understood as including only a, only b, only c, both a and b, both a and c, both b and c, or all of a, b, and c.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

FIG. 1 is a block diagram illustrating a spectrum measurement apparatus according to an exemplary embodiment.

A spectrum measurement apparatus 100 according to an exemplary embodiment may be embedded in an electronic apparatus. Examples of the electronic apparatus may include a cellular phone, a smartphone, a tablet personal computer (PC), a laptop computer, a personal digital assistant (PDA), a portable multimedia player (PMP), a navigation, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device and the wearable device according to exemplary embodiments are not limited thereto.

Referring to FIG. 1, the spectrum measurement apparatus 100 includes a light amount adjuster 110, a light source 120, a light detector 130, and a processor 140.

The light amount adjuster 110 may adjust the magnitude of a light amount output from all or some of a plurality of light sources 121 and 122, by adjusting the strength of an electric signal (e.g., voltage or current) to be applied to all or some of the plurality of light sources 121 and 122 according to a control signal of the processor 140.

The light source 120 may include a plurality of light sources which emit light of different wavelengths to a sample. In an exemplary embodiment, each of the plurality of light sources 121 and 122 may emit near-infrared ray (NIR) or mid-infrared ray (MIR) of different wavelength ranges. However, wavelengths of light emitted by the plurality of light sources 121 and 122 may vary depending on the purpose of measurement or types of composition to be analyzed. Each of the plurality of light sources 121 and 122 may be configured as a single light emitting body, or alternatively, may be configured as a group of a plurality of light emitting bodies. In an exemplary embodiment, the plurality of light sources 121 and 122 may include a light emitting diode (LED), a laser diode, or the like, but this is only exemplary, and the plurality of light sources 121 and 122 are not limited thereto.

In addition, the light source 120 may further include at least one optical element which directs light, emitted by each of the plurality of light sources 121 and 122, toward a desired position of a sample.

The light detector 130 receives light reflected or scattered from or transmitted through the sample among the lights emitted by the plurality of light sources 121 and 122, and may measure the intensity of the received light. In this case, the light detector 130 may amplify the received light according to a predetermined gain. In an exemplary embodiment, the light detector 130 may include a photo diode, a photo transistor (PTr), a charge-coupled device (CCD), or the like. The light detector 130 may be configured as a single element, or alternatively, may be configured as an array having a plurality of elements.

The processor 140 may determine a strength (hereinafter referred to as an optimal strength) of an electric signal to be applied to the plurality of light sources 121 and 122 by using one of the plurality of light sources 121 and 122 to measure the spectrum of a sample. Further, the processor 140 may measure the spectrum of the sample by controlling the light amount adjuster 110 to apply the electric signal having the optimal strength to each of the plurality of light sources 121 and 122 (or all or some of the plurality of light sources 121 and 122).

Hereinafter, an exemplary embodiment of the processor 140 will be described in detail with reference to FIG. 2.

Figure 2:
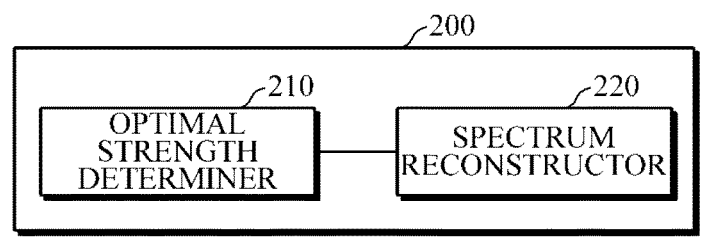
FIG. 2 is a block diagram illustrating a processor included in a spectrum measurement apparatus according to an exemplary embodiment.

FIG. 2 is a block diagram illustrating a processor included in a spectrum measurement apparatus according to an exemplary embodiment. The processor 200 of FIG. 2 may be an example of the processor 140 of FIG. 1.

Referring to FIGS. 1 and 2, the processor 200 includes an optimal strength determiner 210 and a spectrum reconstructor 220.

The optimal strength determiner 210 may select the light source 121, having a larger (or largest) amount of light, between the plurality of light sources 121 and 122. Here, information on the light source (e.g., 121) having a larger amount of light between the plurality of light sources 121 and 122, which is pre-stored in at least one of an internal database and an external database, may be obtained from the database; or may be obtained by applying an electric signal of equal strength to each of the plurality of light sources 121 and 122 and by measuring an amount of light output from each of the plurality of light sources 121 and 122.

The optimal strength determiner 210 may control the light amount adjuster 110 to apply an electric signal of various strengths to the light source 121 having the larger amount of light, and may obtain various levels of intensity measured for a sample by the light detector 130 corresponding to the light source 121, to which the electric signal having various strengths is applied. For example, the optimal strength determiner 210 may obtain the intensity measured for the sample by controlling the light amount adjuster 110 to increase the strength of current, applied to the light source 121 having the larger amount of light, by a predetermined increment starting from 1 mA. In this case, the initial current of 1 mA is merely exemplary and is not limited thereto, and a value of the predetermined increment may vary depending on the performance and usage of a system.

Based on the measured intensity of the light detector 130 according to the strength of the electric signal applied to the light source 121, the optimal strength determiner 210 may determine a strength range of the electric signal in which the light detector 130 is not saturated, and may determine a highest value in the strength range of the electric signal, in which the light detector 130 is not saturated, to be an optimal strength of the electric signal to be applied to the plurality of light sources 121 and 122 to measure the spectrum of the sample. For example, upon applying a current to the light source 121 while increasing the current by an increment of 10 mA starting from 10 mA, and determining based on the intensity measured for the sample by the light detector 130, in the case where the light detector 130 is saturated at 300 mA, the optimal strength determiner 210 may determine a range of 10 mA to 290 mA to be a strength range of the electric signal in which the light detector 130 is not saturated; and may determine the highest value 290 mA, among the values in the range of 10 mA to 290 mA, to be the optimal strength of the electric signal to be applied to the plurality of light sources 121 and 122 to measure the spectrum of the sample.

The spectrum reconstructor 220 controls the light amount adjuster 110 to apply the electric signal of the optimal strength to the plurality of light sources 121 and 122, and may obtain the intensity measured for the sample by the light detector 130 corresponding to each of the plurality of light sources 121 and 122.

The spectrum reconstructor 220 may obtain the spectrum of the sample through a spectrum reconstruction process by using the measured intensity of the light detector 130 and a light spectrum corresponding to each of the plurality of light sources 121 and 122. In this case, the light spectrum is the spectrum of light emitted from each of the plurality of light sources 121 and 122 when the electric signal having various strengths is applied to each of the plurality of light sources 121 and 122. Information on the light spectrum, which is pre-stored in at least one of an internal database and an external database, may be obtained from the database; or may be obtained as the processor 200 controls the light amount adjuster 110 to apply the electric signal having various strengths to each of the plurality of light sources 121 and 122, and measures the intensity of light emitted from each of the plurality of light sources 121 and 122 according to the electric signal having various strengths.

In an exemplary embodiment, the spectrum reconstructor 220 may obtain the spectrum of the sample by using the following Equation 1.

$$R=[S_i \times S_{PD}]^{-1} \times M_{PD} \qquad \text{[Equation 1]}$$

R Here, is the spectrum of the sample, $S_i$ is the light spectrum, $S_{PD}$ is the sensitivity of each wavelength of the light detector, and $M_{PD}$ is the measured intensity of the light detector.

Figure 3:
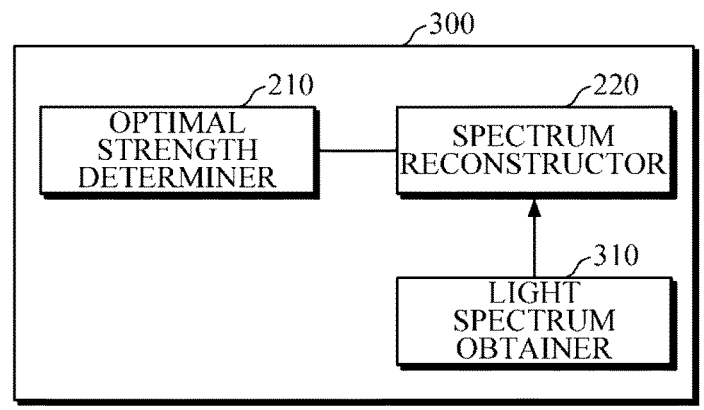
FIG. 3 is a block diagram illustrating a processor included in a spectrum measurement apparatus according to another exemplary embodiment.

FIG. 3 is a block diagram illustrating a processor included in a spectrum measurement apparatus according to another exemplary embodiment. The processor 300 of FIG. 3 may be an example of the processor 140 of FIG. 1.

Referring to FIGS. 1 and 3, the processor 300 includes an optimal strength determiner 210, a spectrum reconstructor 220, and a light spectrum obtainer 310. Here, the optimal strength determiner 210 and the spectrum reconstructor 220 are the same as those described above with reference to FIG. 2, such that detailed description thereof will be omitted.

The light spectrum obtainer 310 may obtain a light spectrum by controlling the light amount adjuster 110 to apply the electric signal having various strengths to each of the plurality of light sources 121 and 122, and by measuring the intensity of light emitted from each of the plurality of light sources 121 and 122 according to the electric signal having various strengths.

Figure 4:
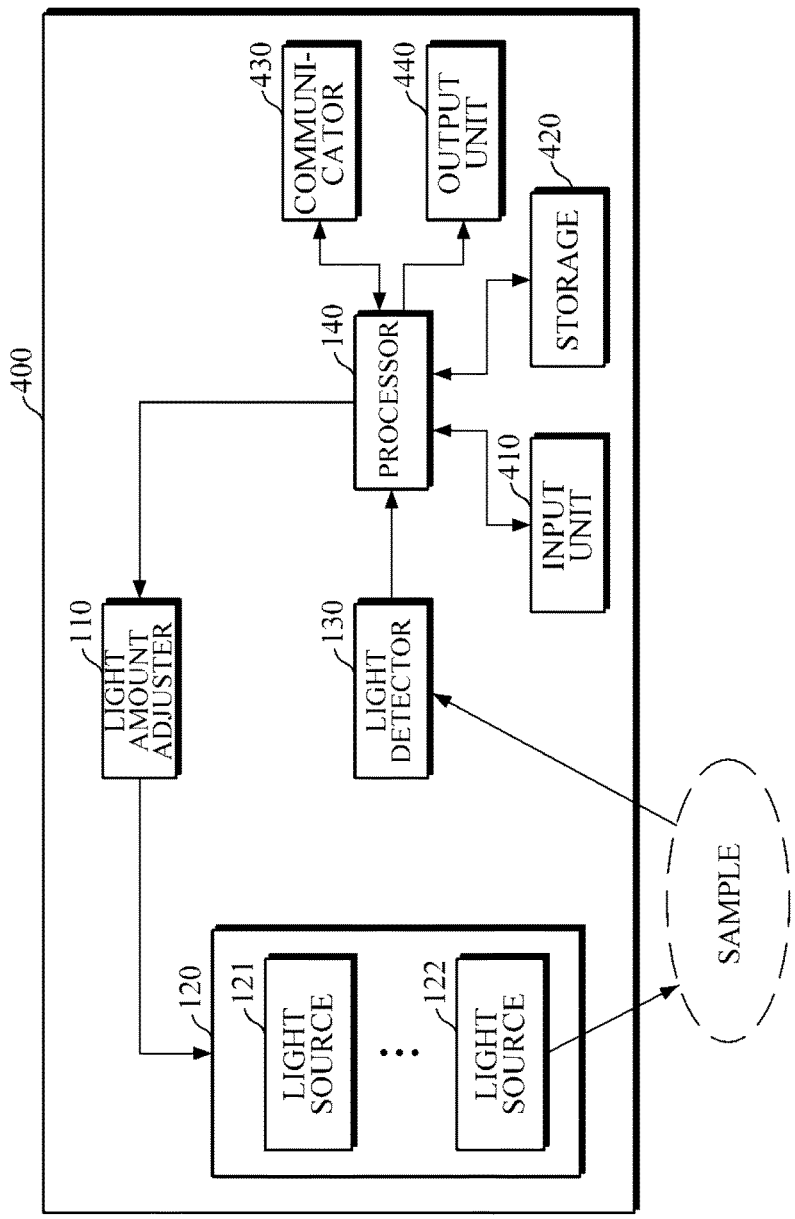
FIG. 4 is a block diagram illustrating a spectrum measurement apparatus according to another exemplary embodiment.

FIG. 4 is a block diagram illustrating a spectrum measurement apparatus according to another exemplary embodiment.

A spectrum measurement apparatus 400 according to another exemplary embodiment may be embedded in an electronic apparatus. Examples of the electronic apparatus may include a cellular phone, a smartphone, a tablet PC, a laptop computer, a personal digital assistant (PDA), a portable multimedia player (PMP), a navigation, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device and the wearable device according to exemplary embodiments are not limited to the above examples.

Referring to FIG. 4, the spectrum measurement apparatus 400 includes a light amount adjuster 110, a plurality of light sources 121 and 122, a light detector 130, a processor 140, an input unit 410, a storage 420, a communicator 430, and an output unit 440. Here, the light amount adjuster 110, the plurality of light sources 121 and 122, the light detector 130, and the processor 140 are the same as those described above with reference to FIGS. 1 to 3, such that detailed description thereof will be omitted.

The input unit 410 may receive various operation signals from a user. In an exemplary embodiment, the input unit 410 may include, for example, a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 420 may store programs or commands for operation of the spectrum measurement apparatus 400, and may store data input to and output from the spectrum measurement apparatus 400. Further, the storage 420 may store data of intensity measured by the light detector 130, spectrum data of a sample that is obtained by the processor 140, information on a light source (e.g., 121) having a larger amount of light between the plurality of light sources 121 and 122, data of the light spectrum, and the like.

The storage 420 may include at least one storage medium of a flash memory type memory, a hard disk type memory, a multimedia card micro type memory, a card type memory (e.g., a secure digital (SD) memory, an extreme digital (XD) memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like. Further, the spectrum measurement apparatus 400 may operate an external storage medium, such as web storage and the like, which performs a storage function of the storage 420 on the Internet.

The communicator 430 may perform communication with an external device. For example, the communicator 430 may transmit, to the external device, data input by a user through the input unit 410, the data of intensity measured by the light detector 130, the spectrum data of a sample that is obtained by the processor 140, the information on a light source (e.g., 121) having a larger amount of light between the plurality of light sources 121 and 122, the data of the light spectrum, and the like; or the communicator 430 may receive various data, which may be useful for spectrum measurement, from the external device.

In this case, the external device may be medical equipment, using the data of intensity measured by the light detector 130, the spectrum data of a sample that is obtained by the processor 140, the information on a light source (e.g., 121) having a larger amount of light between the plurality of light sources 121 and 122, the data of the light spectrum, and the like, a printer to print out results, or a display device which displays in vivo signal data or feature points of the in vivo signal. In addition, examples of the external device may include a digital television (TV), a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 430 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and the communication according to exemplary embodiments is not limited thereto.

The output unit 440 may output the data of intensity measured by the light detector 130, the spectrum data of a sample that is obtained by the processor 140, the information on a light source (e.g., 121) having a larger amount of light between the plurality of light sources 121 and 122, the data of the light spectrum, and the like. In an exemplary embodiment, the output unit 440 may output the data of intensity measured by the light detector 130, the spectrum data of a sample that is obtained by the processor 140, the information on a light source (e.g., 121) having a larger amount of light between the plurality of light sources 121 and 122, the data of the light spectrum, and the like, by using at least one of an acoustic method, a visual method, and a tactile method. To this end, the output unit 440 may include a display, a speaker, a vibrator, and the like.

Figure 5:
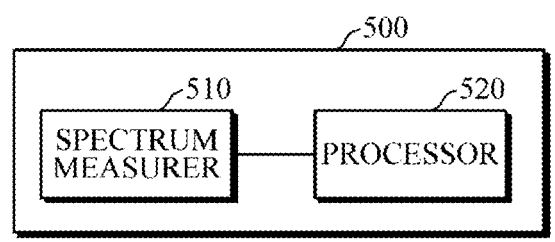
FIG. 5 is a block diagram illustrating a composition analysis apparatus according to an exemplary embodiment.

FIG. 5 is a block diagram illustrating a composition analysis apparatus according to an exemplary embodiment.

A composition analysis apparatus 500 according to an exemplary embodiment may be embedded in an electronic apparatus. Examples of the electronic apparatus may include a cellular phone, a smartphone, a tablet PC, a laptop computer, a personal digital assistant (PDA), a portable multimedia player (PMP), a navigation, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device and the wearable device according to exemplary embodiments are not limited thereto.

Referring to FIG. 5, the composition analysis apparatus 500 includes a spectrum measurer 510 and a processor 520. Here, the spectrum measurer 510 is the same as the spectrum measurement apparatuses 100 and 400 described above with reference to FIGS. 1 to 4, and detailed description thereof will be omitted.

The processor 520 may analyze the composition of a sample by analyzing a spectrum of the sample that is measured by the spectrum measurer 510. Here, the composition may include blood glucose, triglyceride, cholesterol, and the like, but is not limited thereto. For example, the composition may vary depending on the types of the sample.

In an exemplary embodiment, the processor 520 may analyze the composition of the sample by using, for example, near-infrared absorption spectrum analysis or Raman analysis.

The near-infrared absorption spectrum analysis is a method of predicting a blood glucose level by radiating broadband near-infrared light to a sample, analyzing light emitted again to the outside of the sample by diffused reflection, and by calculating an amount of light absorbed by blood glucose molecules in the sample. The Raman analysis is a method of analyzing a blood glucose level using a Raman shift obtained by emitting laser to a sample and by analyzing a wavelength of light emitted from the sample. The Raman analysis exploits scattering, particularly inelastic scattering, in which light incident into the sample collides with atoms or molecules in the sample and is scattered in all directions. The scattered light is not light which is simply reflected from the surface of the atoms or molecules, but light which is scattered after being absorbed by the atoms or molecules, and the scattered light has a wavelength which is longer than a wavelength of the incident light. Such difference in wavelength may be equal to or lower than approximately 200 nm. By analyzing a spectrum of the scattered light, various properties, such as the vibration and structure of molecules in the sample and the like, may be identified.

The spectrum measurer 510 and the processor 520 may be connected to each other by wire or wirelessly. For example, the composition analysis apparatus 500 may be a small portable device having the spectrum measurer 510 and the processor 520 which are connected by wire. Alternatively, the processor 520 may be embedded in a mobile terminal to communicate wirelessly with the spectrum measurer 510.

Figure 6:
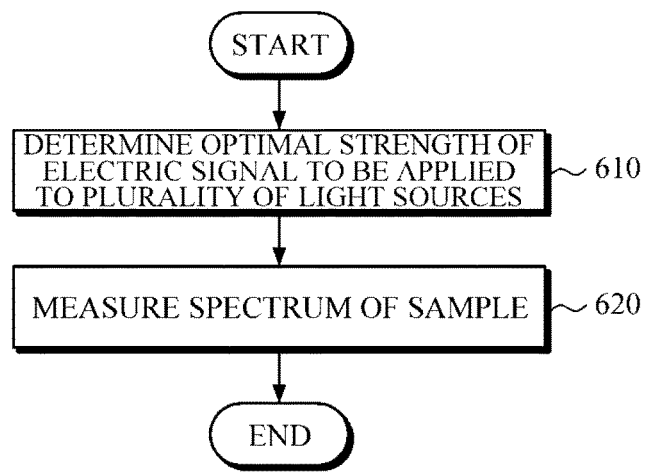
FIG. 6 is a flowchart illustrating a spectrum measurement method according to an exemplary embodiment.

FIG. 6 is a flowchart illustrating a spectrum measurement method according to an exemplary embodiment. The spectrum measurement method of FIG. 6 may be performed by the spectrum measurement apparatus 100 or the spectrum measurement apparatus 400.

Referring to FIGS. 1 and 6, the spectrum measurement apparatus 100 may determine an optimal strength of an electric signal to be applied to the plurality of light sources 121 and 122 by using one of the plurality of light sources 121 and 122 to measure a spectrum of a sample in operation 610.

The spectrum measurement apparatus 100 may obtain the spectrum of the sample by applying the electric signal of the determined optimal strength to each of the plurality of light sources 121 and 122 in operation 620.

Figure 7:
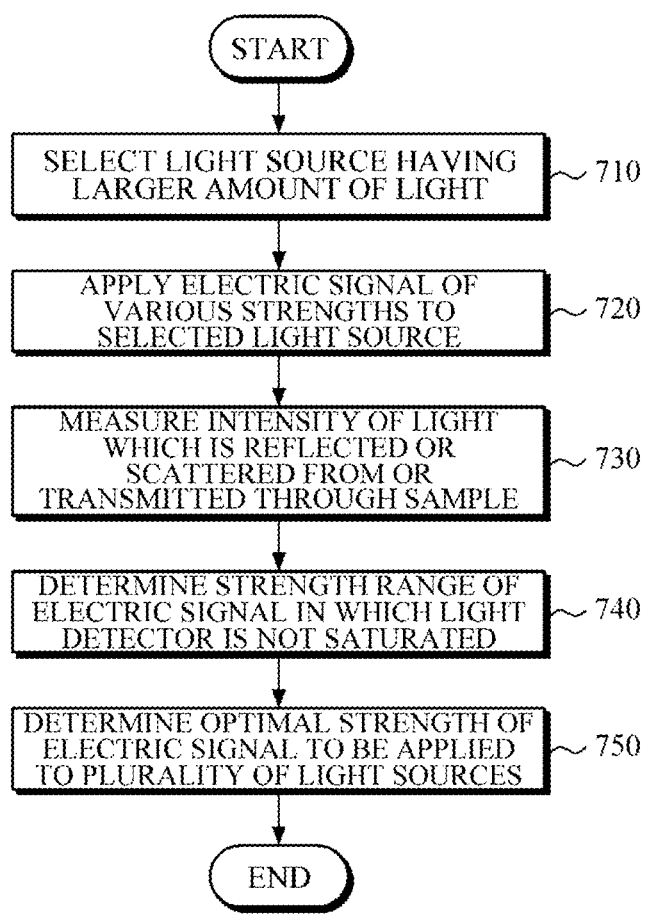
FIG. 7 is a flowchart illustrating determining strength of an electric signal according to an exemplary embodiment.

FIG. 7 is a flowchart illustrating an example of determining strength of an electric signal according to an exemplary embodiment.

Referring to FIGS. 1 and 7, the spectrum measurement apparatus 100 may select the light source 121 having a larger amount of light between the plurality of light sources 121 and 122 in operation 710. Here, information on the light source (e.g., 121) having a larger amount of light between the plurality of light sources 121 and 122, which is pre-stored in at least one of an internal database and an external database, may be obtained from the database; or may be obtained by applying an electric signal of equal strength to each of the plurality of light sources 121 and 122 and by measuring an amount of light output from each of the plurality of light sources 121 and 122.

The spectrum measurement apparatus 100 may emit light to the sample by applying an electric signal of various strengths to the light source 121 having the larger amount of light in operation 720, and may measure the intensity of light which is reflected or scattered from or transmitted through the sample in operation 730.

Based on the measured intensity of the light detector 130 according to the strength of the electric signal applied to the light source 121, the spectrum measurement apparatus 100 may determine a strength range of the electric signal in which the light detector 130 is not saturated in 740, and may determine a highest value in the strength range of the electric signal, in which the light detector 130 is not saturated, to be an optimal strength of the electric signal to be applied to the plurality of plurality of light sources 121 and 122 to measure the spectrum of the sample in operation 750.

Figure 8:
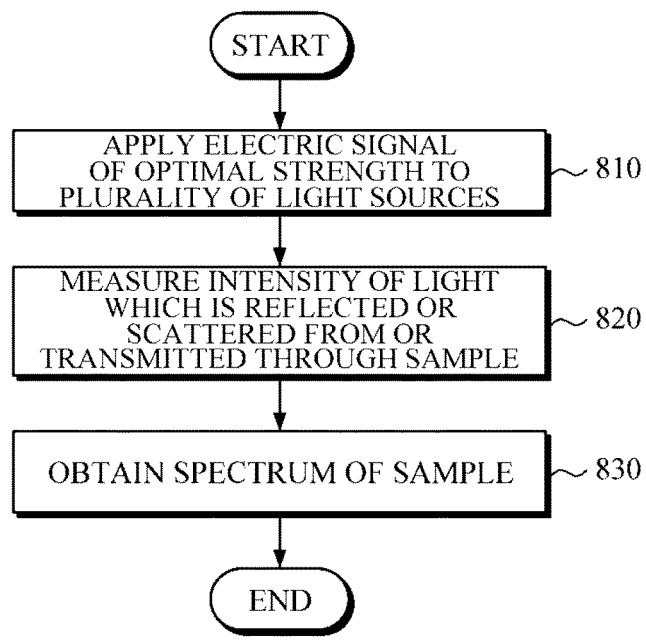
FIG. 8 is a flowchart illustrating obtaining a spectrum of a sample according to an exemplary embodiment.

FIG. 8 is a flowchart illustrating an example of obtaining a spectrum of a sample according to an exemplary embodiment.

Referring to FIGS. 1 and 8, the spectrum measurement apparatus 100 may apply an electric signal of an optimal strength to the plurality of light sources 121 and 122, may emit light to a sample in operation 810, and may measure the intensity of light which is reflected or scattered from or transmitted through the sample in operation 820.

The spectrum measurement apparatus 100 may obtain the spectrum of the sample through a spectrum reconstruction process by using the measured intensity of the light detector 130 corresponding to each of the plurality of light sources 121 and 122, and a light spectrum in operation 830. In an exemplary embodiment, the spectrum measurement apparatus 100 may obtain the spectrum of the sample by using Equation 1 as discussed above.

Figure 9:
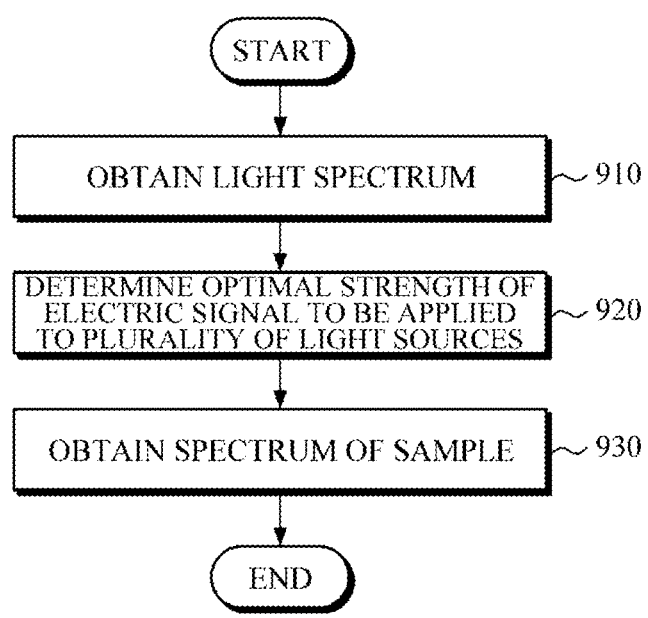
FIG. 9 is a flowchart illustrating a spectrum measurement method according to another exemplary embodiment.

FIG. 9 is a flowchart illustrating a spectrum measurement method according to another exemplary embodiment. The spectrum measurement method of FIG. 9 may be performed by the spectrum measurement apparatus 100 or the spectrum measurement apparatus 400.

Referring to FIGS. 1 and 9, the spectrum measurement apparatus 100 may obtain a light spectrum in 910. For example, the spectrum measurement apparatus 100 may obtain the light spectrum from at least one of an internal database and an external database, or may obtain the light spectrum by applying an electric signal having various strengths to each of the plurality of light sources 121 and 122 and by measuring the intensity of light emitted from each of the plurality of light sources 121 and 122 according to the electric single having various strengths.

The spectrum measurement apparatus 100 may determine an optimal strength of the electric signal to be applied to the plurality of light sources 121 and 122 by using one of the plurality of light sources 121 and 122 to measure the spectrum of the sample in 910.

The spectrum measurement apparatus 100 may obtain the spectrum of the sample by applying the electric signal of the optimal strength to each of the plurality of light sources 121 and 122 in 920.

Figure 10:
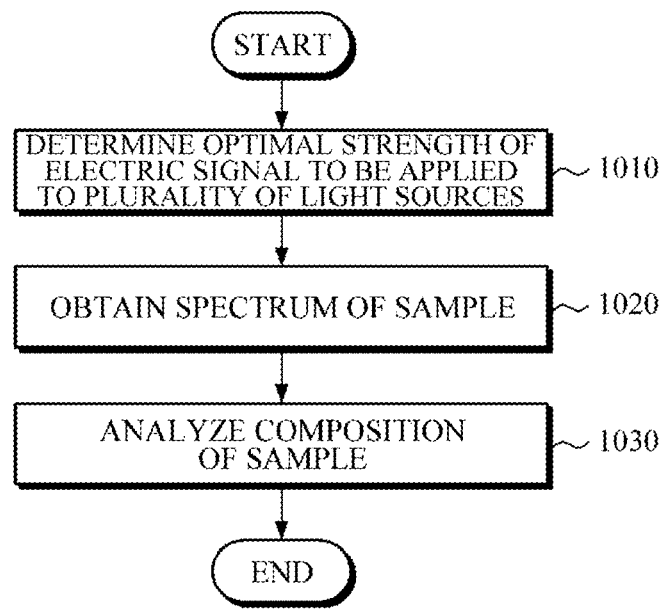
FIG. 10 is a block diagram illustrating a composition analysis method according to an exemplary embodiment.

FIG. 10 is a block diagram illustrating a composition analysis method according to an exemplary embodiment. The composition analysis method may be performed by the composition analysis apparatus of FIG. 5.

Referring to FIGS. 5 and 10, a composition analysis apparatus 500 according to an exemplary embodiment may determine an optimal strength of an electric signal to be applied to the plurality of light sources 121 and 122 by using one of the plurality of light sources to measure the spectrum of the sample in operation 1010.

The composition analysis apparatus 500 may obtain the spectrum of the sample by applying the electric signal of the optimal strength to each of the plurality of light sources 121 and 122 in operation 1020.

The composition analysis apparatus 500 may analyze the composition of the sample by analyzing the spectrum of the sample in 1030. Here, the composition may include blood glucose, triglyceride, cholesterol, and the like, but is not limited thereto. That is, the composition may vary depending on the types of the sample. In an exemplary embodiment, the composition analysis apparatus 500 may analyze the composition of the sample by using near-infrared absorption spectrum analysis or Raman analysis.

Figure 11:
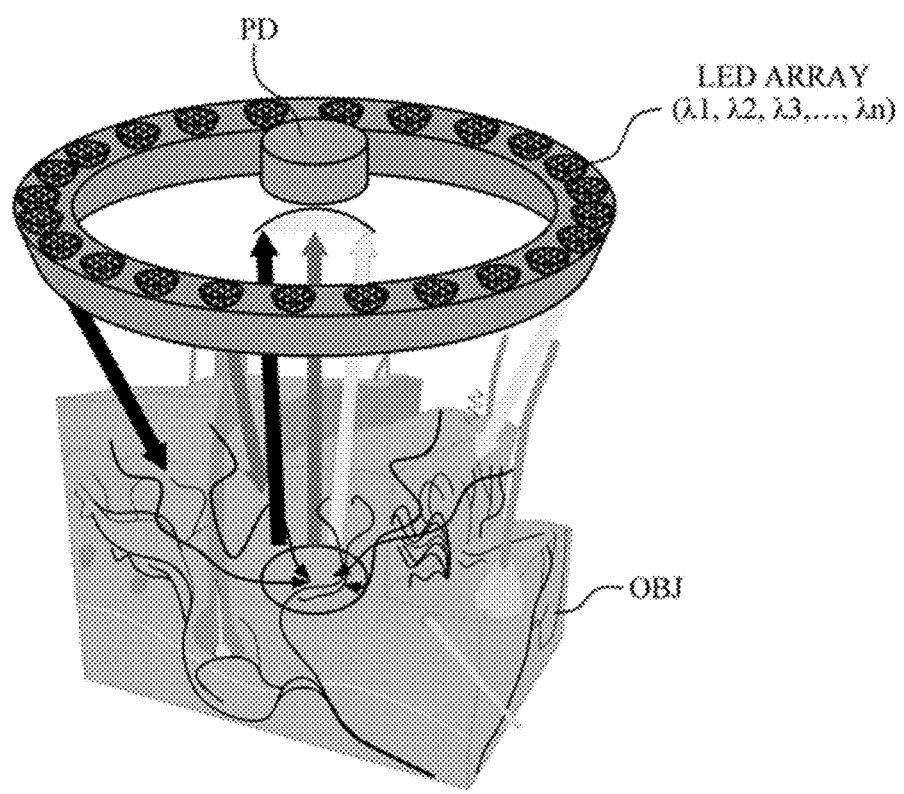
FIG. 11 is a diagram illustrating a light emitting diode (LED)-photo-diode (PD) structure according to an exemplary embodiment.

FIG. 11 is a diagram illustrating an example of an LED-photo diode (PD) structure. The LED-PD structure may be an example of a structure of the light source 120 and the light detector 130 of FIG. 1.

Referring to FIG. 11, the LED-PD structure may include an LED array having n number of LEDs, and one photo diode, in which a peak wavelength of each LED may be set to $\lambda_1, \lambda_2, \lambda_3, \ldots,$ and $\lambda_n$.

The LEDs are sequentially operated according to a predetermined control signal to emit light, having the set peak wavelength, to an object OBJ, and the photo diode PD detects light returning from the object OBJ.

The exemplary embodiments can be realized as a computer-readable code written on a computer-readable recording medium. Codes and code segments to provide the apparatuses and the methods according to exemplary embodiments can be easily deduced by computer programmers of ordinary skill in the art. The computer-readable recording medium may be any type of recording device in which data is stored in a computer-readable manner.

Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

At least one of the components, elements, modules or units represented by a block as illustrated in the drawings may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

The "unit" or "module" used herein may be a hardware component such as a processor or a circuit, and/or a software component that is executed by a hardware component such as a processor.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A spectrum measurement apparatus comprising:
   a plurality of light sources configured to emit light having different wavelengths to an object;
   a light detector configured to receive light, which is reflected or scattered from or transmitted through the object, and to measure an intensity of the received light; and
   a processor configured to determine a strength of an electric signal to be applied to at least one of the plurality of light sources by using one of the plurality of light sources, and to obtain a spectrum of the object by applying the electric signal having the determined strength to the at least one of the plurality of light sources, wherein the processor is further configured to select a light source, having a largest amount of light, among the plurality of light sources, and to determine the strength of the electric signal to be applied to the at least one of the plurality of light sources by using the selected light source.

2. The spectrum measurement apparatus of claim 1, wherein the light detector is further configured to amplify the received light according to a predetermined gain.

3. The spectrum measurement apparatus of claim 1, wherein the processor is further configured to, based on the measured intensity of the light detector that is obtained by applying the electric signal having various strengths to the selected light source, determine a range of the strength of the electric signal in which the light detector is not saturated, and determine a highest value in the range of the strength of the electric signal to be the strength of the electric signal to be applied to the at least one of the plurality of light sources.

4. The spectrum measurement apparatus of claim 1, wherein the processor is further configured to obtain the measured intensity of the light detector, which corresponds to each of the plurality of light sources, by applying the electric signal having the determined strength to each of the plurality of light sources, to obtain a light spectrum corresponding to each of the plurality of light sources, and to obtain the spectrum of the object based on the measured intensity and the light spectrum corresponding to each of the plurality of light sources.

5. The spectrum measurement apparatus of claim 4, wherein the light spectrum corresponding to each of the plurality of light sources is a spectrum of light emitted from each of the plurality of light sources when the electric signal having various strengths is applied to each of the plurality of light sources.

6. The spectrum measurement apparatus of claim 4, wherein the processor is further configured to obtain the light spectrum corresponding to each of the plurality of light sources from at least one of an internal database and an external database, or to obtain the light spectrum corresponding to each of the plurality of light sources by applying the electric signal having various strengths to each of the plurality of light sources and measuring the intensity of light emitted from each of the plurality of light sources.

7. The spectrum measurement apparatus of claim 1, further comprising a light amount adjuster configured to adjust the strength of the electric signal to be applied to the at least one of the plurality of light sources according to a control signal of the processor.

8. A spectrum measurement method of a spectrum measurement apparatus comprising a plurality of light sources and a light detector, the spectrum measurement method comprising:

determining a strength of an electric signal to be applied to at least one of the plurality of light sources by using one of the plurality of light sources; and obtaining a spectrum of an object by applying the electric signal having the determined strength to the at least one of the plurality of light sources, wherein the determining the strength of the electric signal to be applied to the at least one of the plurality of light sources comprises selecting a light source, having a largest amount of light, among the plurality of light sources, and determining the strength of the electric signal to be applied to the at least one of the plurality of light sources by using the selected light source.

9. The spectrum measurement method of claim 8, wherein the determining the strength of the electric signal to be applied to the plurality of light sources further comprises:

emitting light to the object by applying the electric signal having various strengths to the selected light source, and measuring, by the light detector, an intensity of light reflected or scattered from or transmitted through the object;

based on the measured intensity, determining a range of the strength of the electric signal in which the light detector is not saturated; and determining a highest value in the range of the strength of the electric signal to be the strength of the electric signal to be applied to the at least one of the plurality of light sources.

10. The spectrum measurement method of claim 8, wherein the obtaining the spectrum of the object comprises:

emitting light to the object by applying the electric signal having the determined strength to the at least one of the plurality of light sources, and measuring, by the light detector, an intensity of the light reflected or scattered from or transmitted through the object; and obtaining the spectrum of the object by using the measured intensity and a light spectrum corresponding to each of the plurality of light sources.

11. The spectrum measurement method of claim 10, wherein the light spectrum corresponding to each of the plurality of light sources is a spectrum of light emitted from each of the plurality of light sources when the electric signal having various strengths is applied to each of the plurality of light sources.

12. The spectrum measurement method of claim 10, further comprising obtaining the light spectrum corresponding to each of the plurality of light sources from at least one of an internal database and an external database.

13. The spectrum measurement method of claim 10, further comprising:

applying the electric signal having various strengths to each of the plurality of light sources; and obtaining the light spectrum corresponding to each of the plurality of light sources by measuring the intensity of light emitted from each of the plurality of light sources.

14. A composition analysis apparatus comprising:

a spectrum measurer configured to obtain a spectrum of an object; and a first processor configured to analyze the spectrum of the object to analyze a composition of the object, wherein the spectrum measurer comprises:

a plurality of light sources configured to emit light having different wavelengths to the object;

a light detector configured to receive light, which is reflected or scattered from or transmitted through the object, and to measure an intensity of the received light; and a second processor configured to determine a strength of an electric signal to be applied to at least one of the plurality of light sources by using one of the plurality of light sources, and to obtain the spectrum of the object by applying the electric signal having the determined strength to the at least one of the plurality of light sources, wherein the second processor is further configured to select a light source, having a largest amount of light, among the plurality of light sources, and to determine the strength of the electric signal to be applied to the at least one of the plurality of light sources by using the selected light source.

* * * * *